(12) United States Patent
Bierhoff et al.

(10) Patent No.: US 9,687,156 B2
(45) Date of Patent: Jun. 27, 2017

(54) NEEDLE DEVICE WITH AN OPTICAL FIBER INTEGRATED IN A MOVABLE INSERT

(75) Inventors: Waltherus Cornelis Jozef Bierhoff, Eindhoven (NL); Bernardus Hendrikus Wilhelmus Hendriks, Eindhoven (NL); Franciscus Marinus Antonius Maria Van Gaal, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 195 days.

(21) Appl. No.: 14/342,442

(22) PCT Filed: Sep. 7, 2012

(86) PCT No.: PCT/IB2012/054636
§ 371 (c)(1),
(2), (4) Date: Mar. 3, 2014

(87) PCT Pub. No.: WO2013/035076
PCT Pub. Date: Mar. 14, 2013

(65) Prior Publication Data
US 2014/0213911 A1 Jul. 31, 2014

Related U.S. Application Data

(60) Provisional application No. 61/532,218, filed on Sep. 8, 2011.

(51) Int. Cl.
*A61B 6/00* (2006.01)
*A61B 5/00* (2006.01)

(52) U.S. Cl.
CPC .......... *A61B 5/0084* (2013.01); *A61B 5/6848* (2013.01); *A61B 5/0071* (2013.01);
(Continued)

(58) Field of Classification Search
CPC ... A61B 5/0071; A61B 5/0075; A61B 5/0084; A61B 5/0086; A61B 5/6844; A61B 5/6848
(Continued)

(56) References Cited

U.S. PATENT DOCUMENTS

| 4,566,438 A | 1/1986 | Liese et al. |
| 5,280,788 A | 1/1994 | Janes et al. |

(Continued)

FOREIGN PATENT DOCUMENTS

| WO | 2004016155 A2 | 2/2004 |
| WO | WO2009114653 | 12/2009 |

(Continued)

OTHER PUBLICATIONS

R. Nachabe et al., "Estimation of Lipid and Water Concentrations in Scattered media with Diffuse Optical Spectroscopoy from 900 to 1600 nm", Journal of biomedical Optics 15(3), 1 (May/Jun. 2010), pp. 1-1 through 1-11.

(Continued)

*Primary Examiner* — Sanjay Cattungal

(57) ABSTRACT

A needle device includes a hollow shaft, an elongated insert and an operating lever. The hollow shaft has a first distal end portion with a bevel, the elongated insert has a second distal end portion and is movably arranged within the hollow shaft, and the operating lever is shiftable between a first condition and a second condition. Furthermore, the operating lever is interconnected with the elongated insert such that the second distal end portion is located within the hollow shaft and proximally to the bevel when the operating lever is in the first condition, and that the second distal end portion is located outside the hollow shaft and distally to the bevel when the operating lever is in the second condition.

13 Claims, 7 Drawing Sheets

(52) U.S. Cl.
CPC ............ *A61B 5/0075* (2013.01); *A61B 5/0086* (2013.01); *A61B 5/6844* (2013.01)

(58) Field of Classification Search
USPC ............ 600/473–480, 407, 114, 104; 604/22, 604/164.01, 164.02
See application file for complete search history.

(56) References Cited

U.S. PATENT DOCUMENTS

| | | | |
|---|---|---|---|
| 6,695,772 | B1 | 2/2004 | Bon et al. |
| 7,025,765 | B2 | 4/2006 | Balbierz et al. |
| 7,470,237 | B2 | 12/2008 | Beckman |
| 8,046,057 | B2 * | 10/2011 | Clarke ................ A61B 5/0066 600/129 |
| 2002/0026127 | A1 | 2/2002 | Balbierz et al. |
| 2004/0138528 | A1 * | 7/2004 | Richter .............. A61B 17/3421 600/134 |
| 2005/0026156 | A1 | 2/2005 | Lie et al. |
| 2005/0107706 | A1 | 5/2005 | Zuluaga et al. |
| 2005/0261568 | A1 | 11/2005 | Hular et al. |
| 2006/0030785 | A1 | 2/2006 | Field et al. |
| 2006/0155210 | A1 | 7/2006 | Beckman et al. |
| 2007/0142714 | A1 * | 6/2007 | Shumate ................ A61B 5/01 600/300 |
| 2008/0045842 | A1 | 2/2008 | Furnish |
| 2008/0140006 | A1 * | 6/2008 | Eskuri ..................... A61B 5/00 604/117 |
| 2008/0140091 | A1 | 6/2008 | DeDeyne et al. |
| 2008/0221456 | A1 | 9/2008 | Babchenko |
| 2009/0275840 | A1 | 11/2009 | Roschak et al. |
| 2010/0041949 | A1 * | 2/2010 | Tolkowsky ........... A61B 1/0052 600/109 |
| 2010/0274081 | A1 * | 10/2010 | Okoniewski ....... A61B 17/3474 600/109 |
| 2010/0331782 | A1 | 12/2010 | Hendriks et al. |
| 2012/0088991 | A1 * | 4/2012 | Nachabe .............. A61B 5/0075 600/310 |
| 2012/0184842 | A1 * | 7/2012 | Boularot ............. A61B 5/0068 600/411 |
| 2012/0330101 | A1 * | 12/2012 | Brennan ............ A61B 1/00096 600/177 |
| 2014/0187970 | A1 * | 7/2014 | Suter .................... A61B 5/0066 600/478 |
| 2014/0213911 | A1 | 7/2014 | Bierhoff et al. |

FOREIGN PATENT DOCUMENTS

| | | |
|---|---|---|
| WO | WO2011033390 | 3/2011 |
| WO | WO2011043327 | 4/2011 |

OTHER PUBLICATIONS

Q. Zhang et al., "Turbidity-Free Fluorescence Spectroscopy of Biological Tissue", Optics Letters, vol. 25, No. 19, Oct. 1, 2000, pp. 1451 through 1453.

* cited by examiner

NEEDLE DEVICE WITH AN OPTICAL FIBER INTEGRATED IN A MOVABLE INSERT

CROSS-REFERENCE TO PRIOR APPLICATIONS

This application is the U.S. National Phase application under 35 U.S.C. §371 of International Application Serial No. PCT/IB2012/054636, filed on Sep. 7, 2012, which claims the benefit of U.S. Application Ser. No. 61/532,218, filed on Sep. 8, 2011. These applications are hereby incorporated by reference herein.

FIELD OF THE INVENTION

The invention generally relates to a needle device with integrated fibers. Particularly, the invention relates to a needle device with a movable insert including at least one optical fiber, for optical tissue inspection, e.g. based on diffuse reflectance or autofluorescence measurements to diagnose whether tissue is cancerous or not.

BACKGROUND OF THE INVENTION

In the field of oncology it is important to be able to discriminate tumor tissue from normal tissue. Golden standard is to inspect tissue at the pathology department after a biopsy or after surgical resection. A drawback of this current way of working is that real time feedback during the procedure of taking a biopsy or performing the surgical resection is missing. A way to provide instant feedback in case of, for instance, the biopsy needle is to incorporate fibers to perform optical measurements at the tip of the needle. Various optical methods can be employed with diffuse reflectance (DRS) and autofluorescence measurement as the techniques that are most commonly investigated. Several probes are used to perform these measurements but in general these probes have blunt end surfaces and are therefore not a direct integral part of the needle.

In U.S. Pat. No. 4,566,438 a sharp fiber-optic stylet is described in which two fibers are incorporated that could perform DRS and fluorescence measurements at the tip of the needle. However the fibers in the stylet are bevelled and as a result a significant part of the light in the fiber will undergo total internal reflecton at the tip of the needle, reaching the cladding material of the fiber and then exiting the fiber. This travelling through the buffer can cause a significant amount of unwanted autofluorecence of the cladding material hampering the measurement of the tissue autofluorescence.

SUMMARY OF THE INVENTION

To integrate a fiber into a needle a multilumen concept can be used, hence the needle consist of an outer cannula and an insert, where the insert is for instance made of a multilumen core with the fiber integrated in one of the lumen of the multilumen.

With the attempt to at least alleviate the mentioned drawbacks, the following requirements are preferably fulfilled by a needle according to an embodiment of the invention:

Needle must be sharp.
Integrating the fibers into the needle must not alter the penetration properties into the tissue.
The fibers in the needle may not extend beyond the bevel of the cannula.
The fibers should make good contact with the tissue i.e. voids between fiber end and tissue should be avoided since they can fill up with blood.

Therefore, it is an object of the invention to provide a needle device into wich optical fibers are integrated, such that the above requirements are preferably fulfilled. It might be another object of the invention to provide a system for using the needle device.

These and other objects might be achieved by the subject matter according to the independent claim. Further embodiments of the present invention are described in the dependent claims.

According to the invention, a needle device is proposed comprising a cannula or hollow shaft with a multilumen stylet, i.e. an elongated insert inside. The insert contains at least at the distal end at least one lumen. The cannula has a bevelled end and the distal end of the insert is shaped in such a way that, during insertion, it is not protruding the bevel of the cannula. In the lumen, substantially straight cleaved fibers (i.e angle end face is small such that no total internal reflection at the interface can take place) are present that may be connected at the proximal end to a console. The insert of the needle device may be moved forward after the needle has been inserted in a body. As a result, in this way the insert, and with the insert the distal end of a fiber, is pressed against the tissue and assures a good contact as required.

In general, a needle device according to an embodiment of the invention comprises a hollow shaft, an elongated insert and an operating means. The hollow shaft has a first distal end portion with a bevel, the elongated insert has a second distal end portion and is movably arranged within the hollow shaft, and the operating means is shiftable between a first condition and a second condition. Furthermore, the operating means is interconnected with the elongated insert, so that the second distal end portion is located within the hollow shaft and proximally to the bevel, when the operating means is in the first condition, and that the second distal end portion is located outside the hollow shaft and distally to the bevel, when the operating means is in the second condition.

The tip of the needle device, i.e. the bevel is in general slanted in order to allow easy entry into the tissue. Therefore, with 'bevel' is meant a geometrical structure allowing for introducing the needle into tissue. Usually, a shaft of a needle includes a circular cross section. The distal end of a needle shaft, in particular of a shaft of a hollow needle, is cut such that an oval surface is formed, which is inclined relative to the longitudinal axis of the shaft. Further, there is defined an angle between the longitudinal axis of the shaft and the inclined surface, i.e. the bevel. The bevel forms a pointed tip at the most distal end of the needle. Furthermore, the edge between the outer surface of the shaft and the inclined surface of the bevel might be sharpened.

The wording 'bevel' might also include similar structures at the tip of the needle, which structures are useful for introducing the needle into a tissue. For example, the bevel might be a convex or concave surface, or the bevel might be a combination of several small surfaces, wherein these surfaces are connected to each other by steps or edges. It might also be possible that the cross section of the shaft is not completely cut by the bevel, such that an area remains which is blunt, i.e. is perpendicularly orientated relative to the longitudinal axis of the shaft. Such a 'blunt' end might include rounded edges or might also form a rounded leading edge. As another exemple, a sharp edge might be formed by two or more slanted surfaces being symmetrically or asymmetrically arranged to form the tip of the needle.

In accordance with an embodiment of the invention, the distal end portion of the elongated insert comprises a bevel. The front surface of the insert includes at least one of a beveled portion, a stepped portion and a blunt portion.

It should be noted that the bevel might form an acute angle with the shaft, such that the needle includes a pointed tip. Preferably, the acute angle might be approximately 20°.

The elongated insert of the needle device may be removably arranged within the hollow shaft. That is, the insert may be arranged with its bevel in an appropriate relation to the bevel of the hollow shaft, during an insertion of the needle device into tissue, and after said insertion, the insert may be released and pulled back out of the shaft, so that the hollow shaft may be used for an injection of a substance or a suction of for example a liquid out of a body.

According to a further embodiment of the invention, the elongated insert comprises two channels both with an open end at the bevel of the elongated insert, wherein one open end is located more proximally than the other open end. The needle device may comprise two optical fibers each arranged within one of the channels, wherein the optical fiber which is arranged within the channels with the more proximally located open end may protrude out of the open end. The optical fiber may protrude more than half the diameter of the optical fiber out of the open end of the channel. With such an arrangement of fibers, with the end surfaces of the fibers in close proximity, especially fluorescence measurements are possible with increased signal.

According to another embodiment of the invention, the open ends of the two channels in the insert are located with a distance from each other which is greater than the diameter of the elongated insert. With such an arrangement of the fibers, especially diffuse reflectance spectroscopy is possible with good results. For example, the distance may be more than 1.1 times greater than the diameter. Particularly, the distance may be more than 1.25 times greater than the diameter. Preferably, the distance may be more than 1.5 times greater than the diameter. In other words, the distance between the fiber ends at the tip part of the needle should be as great as possible. It is noted that the distances are measured from the central axis of one of the fibers to the central axis of the other one of the fibers.

According to a further embodiment of the invention, the operating means of the needle device includes elements of at least one of an electromagnetic drive and an electrically driven mechanical drive, so that the movement between the first and second condition may be performed for example due to an electrical contact of a switch element.

According to another embodiment of the invention, the operating means of the needle device includes elements for manually shifting the operating means between the first condition and the second condition, and thus the insert into and out of the distal end of the hollow shaft. The operating means may include a first lever and a second lever, wherein the first lever is pivotable between the first condition and the second condition, and wherein the second lever is arranged between the first lever and the elongated insert, so that a pivot movement of the lever is converted in a translational movement of the elongated insert.

According to another embodiment of the invention, the elongated insert is spring-biased in a direction to a position in which the second distal end portion of the elongated insert is located within the hollow shaft and proximally to the first bevel of the hollow shaft.

To facilitate the movement of the insert inside the hollow shaft, the needle device may further comprise at least one bearing for supporting a translational movement of the elongated insert.

According to yet a further embodiment of the invention, the needle device further comprises a console including a light source, a light detector and a processing unit for processing the signals provided by the light detector, wherein the light source and the light detector are connected with the optical fiber. One of the light source and the light detector may be connected with a first optical fiber and the other one of the light source and the light detector may be connected with a second optical fiber. The light source may be one of a laser, a light-emitting diode or a filtered light source, and the console may further comprise one of a fiber switch, a beam splitter or a dichroic beam combiner.

According to an embodiment of the invention, the system is adapted to perform at least one out of the group consisting of diffuse reflectance spectroscopy, diffuse optical tomography, differential path length spectroscopy, and Raman spectroscopy.

According to another embodiment of the invention, the needle device further comprises a switch for activating optical measurements. The switch may activate the optical measurements, when the operating means is in the second condition. It is noted, that the switch for activating optical measurements and the above mentioned switch for triggering the movement of the insert inside the hollow shaft, may be integrated in a single switch element.

According to another aspect, the shaft and tip of the needle device may be made of metal, wherein the metal might be MRI compatible such as Titanium. The needle tip may also be made of a ceramic material. This has the advantage of being mouldable in various shapes while still allowing for a sharp and robust needle tip. On the other end, a housing of the needle device may be made by plastic injection moulding. The elongated insert may be made of a plastic material and may be coated with a metal coating or a coating having low autofluorescence.

According to a further embodiment of the invention, the hollow shaft of the needle further includes facets formed at both sides of the bevel.

A 'facet' may by a small and plane surface. Usually, a 'facet' may be realized by cutting away a small area of a body thereby achieving a surface with edges to other surfaces of the body. The contour of a facet may be affected by the angle of cutting. Furthermore, the surface of a facet may be convex or concave, i.e. the facet may be curved forming a part-cylindrical shape. The edges of the facet may preferably be sharpened or may be rounded and thus blunt.

Principally, it is possible to introduce a needle or instrument into tissue by cutting the tissue or displacing the tissue. Accordingly, the edges of a needle or instrument will be sharp or smooth. It will be understood that a combination of cutting and displacing or squeesing the tissue is also possible. Depending from the application, the needle or instrument will more or less cut and/or displace.

The invention might also be related to a computer program for the processing unit of the needle device according to the invention. The computer program is preferably loaded into a working memory of a data processor. However, the computer program may also be presented over a network like the worldwide web and may be downloaded into the working memory of a data processor from such a network. The computer program might control the emitting of light, might process the signals coming from the light detector at the proximal end of the detector fiber(s). These data might then be visualized on a monitor.

The aspects defined above and further aspects, features and advantages of the present invention may also be derived from the examples of embodiments to be described hereinafter and are explained with reference to examples of embodiments. The invention will be described in more detail hereinafter with reference to examples of embodiments but to which the invention is not limited.

BRIEF DESCRIPTION OF THE DRAWINGS

The illustration in the drawings is schematically only and not to scale. It is noted that similar elements are provided with the same reference signs in different figures, if appropriate.

DETAILED DESCRIPTION OF EMBODIMENTS

Figure 1:
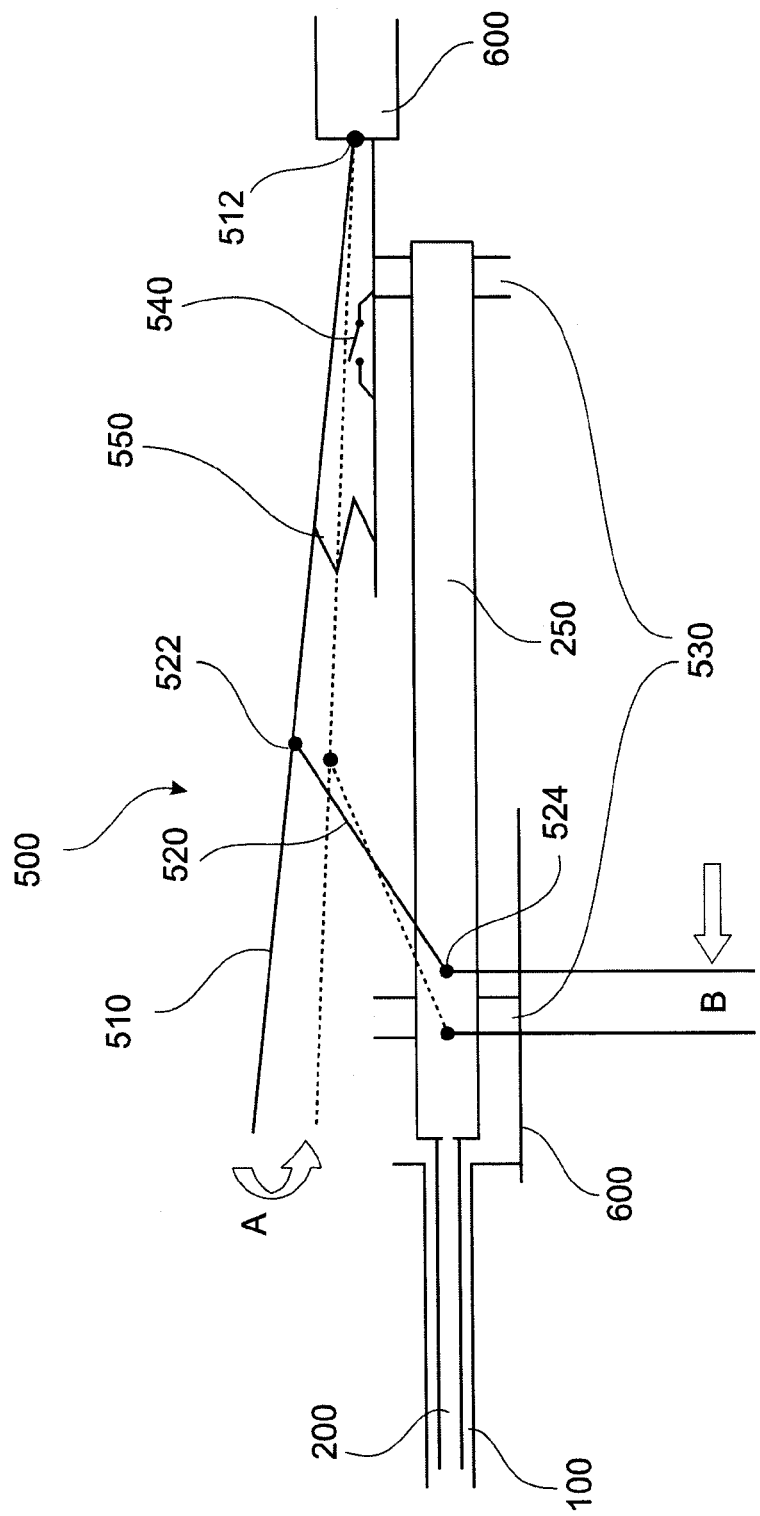
FIG. 1 shows a schematic illustration of an exemplary needle device according to the invention.

To provide a needle device, a multilumen stylet in form of an insert 200 inside a cannula having a hollow shaft 100 is used. The insert 200 is typically made with well defined lumen at positions that define the distance between fibers 300 that can be inserted in these lumen.

According to the invention, the insert 200 has at least one lumen or channel 260 that can contain at least one fiber 300. The insert of the needle device may be moved forward after the needle device has been inserted in a body. Therefore, it is very easy for the surgeon to work with it. The shape is typically like a syringe with an operating mechanism at for example one side of the cylinder of the syringe. The surgeon can introduce the needle into a tissue like a normal injection needle and after insertion push, with one finger, a lever 510 of the operating mechanism 500. By pushing the lever 510, a second lever 520 translates the movement to the insert 200 so that the insert slides from a position with its distal end inside the hollow shaft forward over the length of a cannula pocket at the distal end of the hollow shaft to a second position outside the distal end of the hollow shaft. In this second position of the insert, optical measurements may be performed. By loosening the lever 510, the insert may be retract automatically to the not protruding first position. In this way it is possible to measure at different locations, i.e. at different locations in depth by pushing the needle outwardly, without retracting the needle in total. This is a huge advantage during the measurements.

To push the insert 200 forward a number of constructions are possible. For instance a motorized, most likely electromagnetically, drive or a manually, most likely hand, drive can be implemented. Both could, for example, drive a screw spindle, cam profile, wedge or lever configuration.

Figure 2:
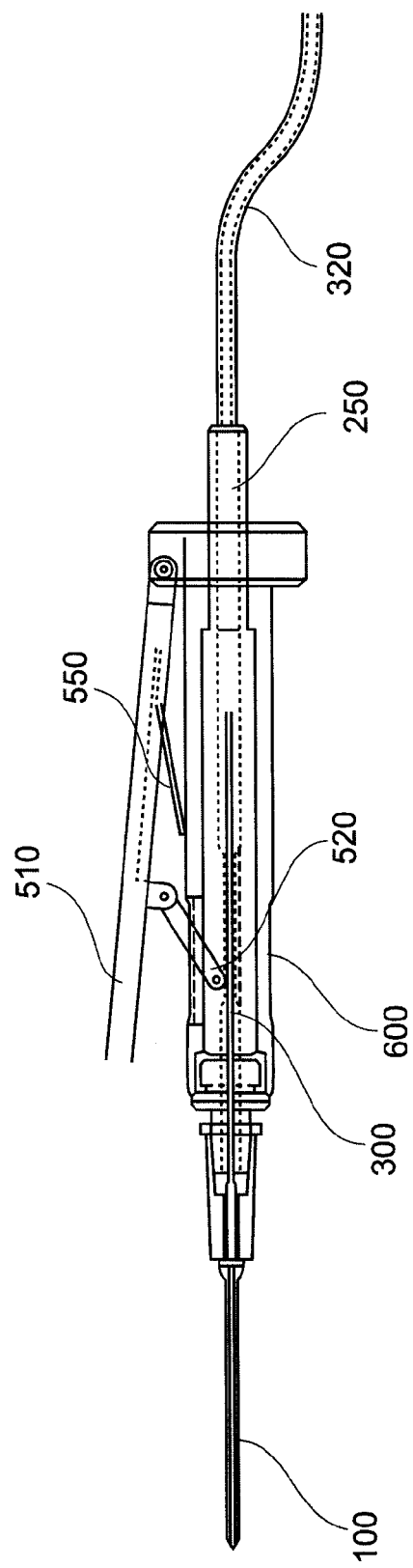
FIG. 2 shows an exemplary needle device according to the invention.

In a preferred embodiment, for simplicity and easy manufacturing, a lever construction as shown in FIGS. 1 and 2 may be used. A first lever 510 comprises a pivot 512 arranged at the housing 600 of the needle device. A second lever 520 comprising a first pivot 522 and a second pivot 524 is arranged between the first lever 510 and the insert 200, to translate the pivotal movement (arrow A) of the first lever in a direction to the housing, into a translational movement (arrow B) of the insert in a direction to the distal end of the needle device. The insert comprises a slider 250 which is adapted to firstly be connected with the second pivot 524 of the second lever 520, and to secondly be guided within the housing 600. As shown in FIG. 1, bearings 530 are provided between the housing 600 and the slider 250. Such a lever construction has a very low friction which is an advantage above the other possible constructions. The lever construction provides the surgeon also with a good "feel" during the measurement. It is important that the surgeon obtains clear feedback, in this case by feeling with his fingertip during the measurement whether the insert is moved forward. This feel can be adjusted, to the wishes of the surgeon, by adjusting the pre-load (spring 550) of the first lever 510. It is noted that the spring 550 may also be arranged at other position appropriate to finally retract the distal end portion of the insert 200 into the hollow shaft 100.

Additionally a switch 540 is provided that may trigger the measurement due to a pushing of the first lever 510.

Figure 3:
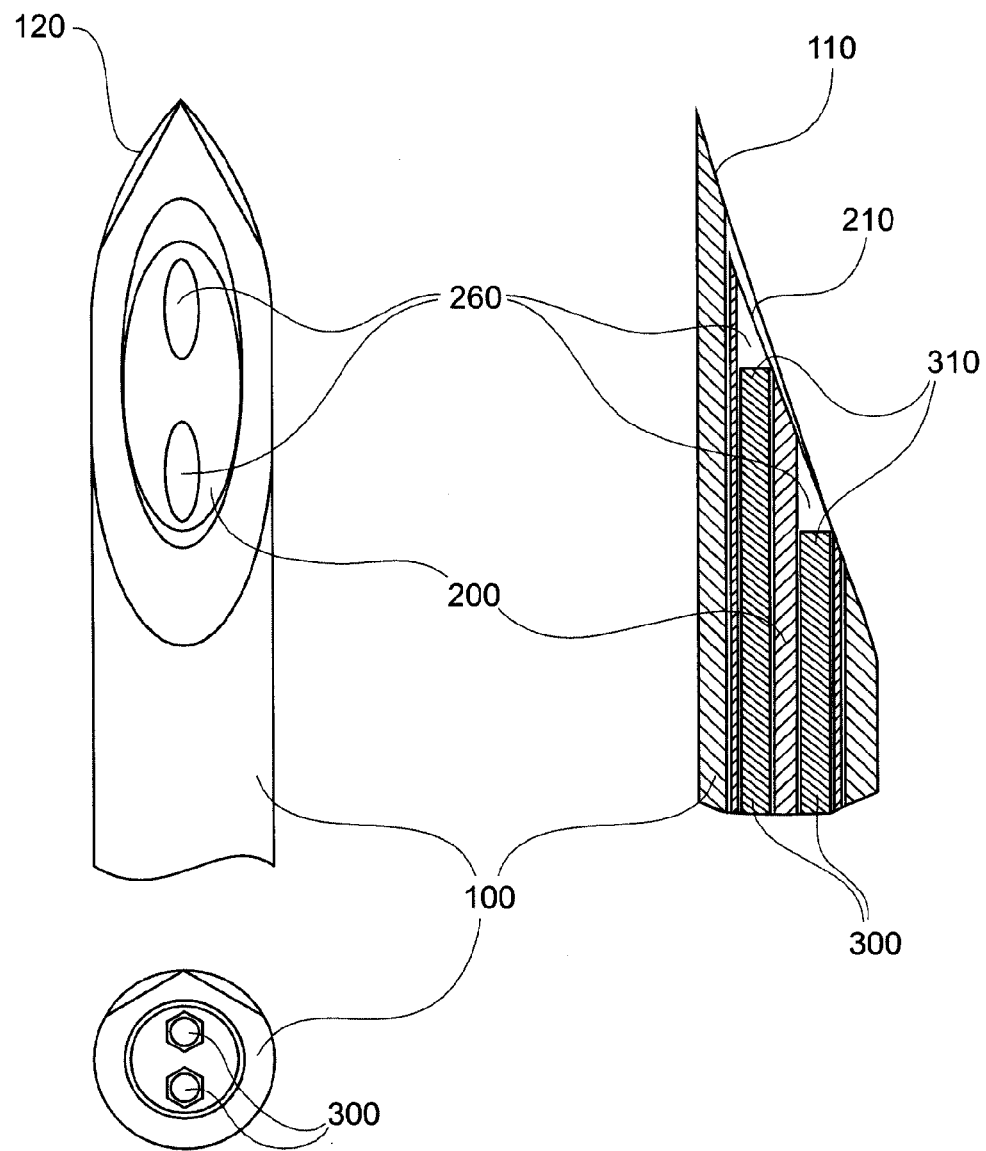
FIG. 3 shows different views of a tip portion of a needle device according to a first embodiment of the invention.

FIG. 3 illustrates a first embodiment of a distal tip portion of a needle devide according to the invention, as a plain view as well as a section side view. The needle comprises a hollow shaft 100 and an elongated insert 200. The shaft 100 is formed with a bevel 110 and the insert 200 is formed with a front surface 210. As can be seen in FIG. 3, the bevel 110 is formed with an angle which is different to the angle of the second bevel 210. The insert 200 further includes channels 260 having open ends at the front surface 210 of the insert. Within the channels 260, optical fibers 300 with front surfaces 310 are arranged.

Figure 4:
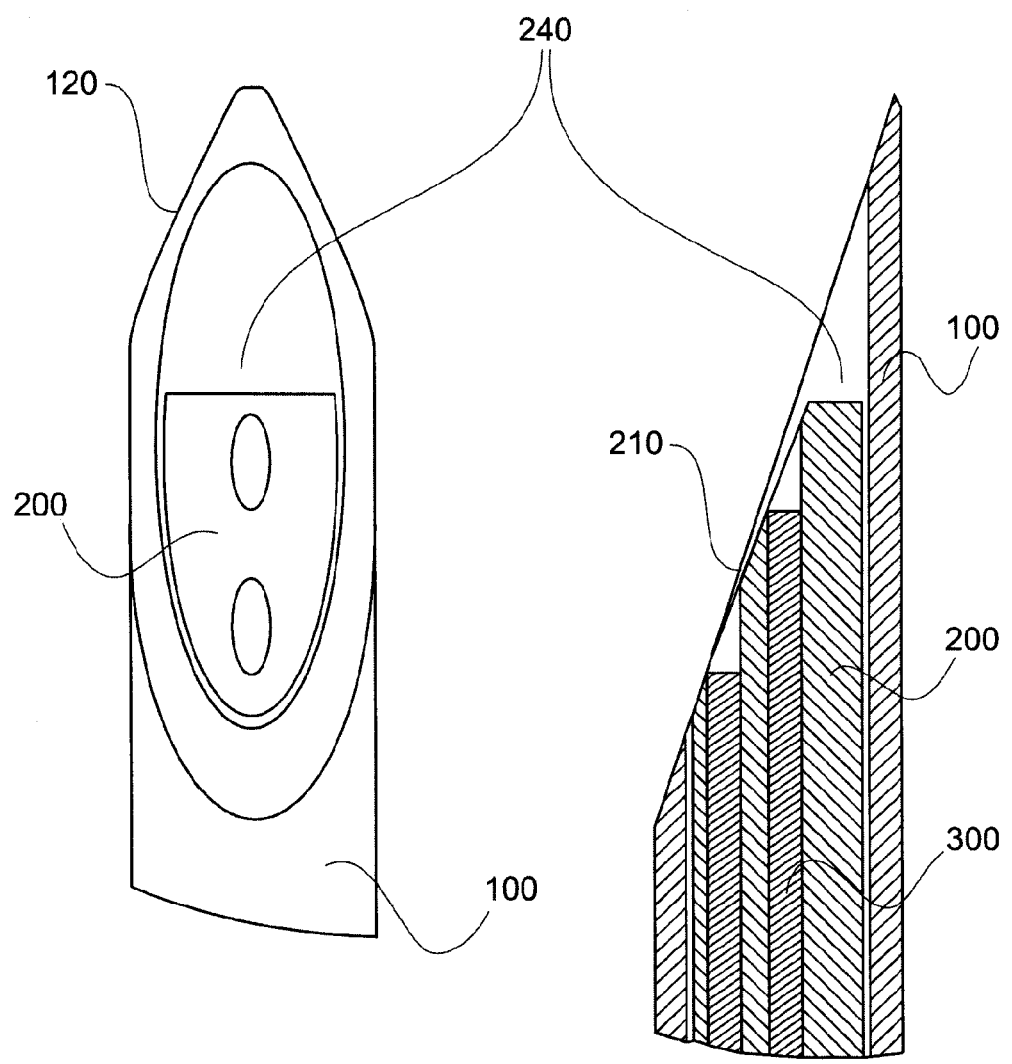
FIG. 4 shows different views of a tip portion of a needle device according to a second embodiment of the invention.

FIG. 4 shows a second embodiment of a distal end portion of a needle device according to the invention. Also in this embodiment, the shaft 100 has facets 120 formed at the sides of the bevel so that the facets are orientated to the front as well as the side of the tip. The insert 200 of this embodiment has a blunt distal tip, i.e. the front surface of the insert 200 includes a bevelled portion 210 and a blunt portion 240. It will be understood that a contact with tissue will differ due to the different distal tip of the insert, when the insert with a distal end portion according to the first embodiment will be pushed out of the hollow shaft, and when the insert with a distal end portion according to the second embodiment will be pushed out of the hollow shaft 100.

Figure 5:
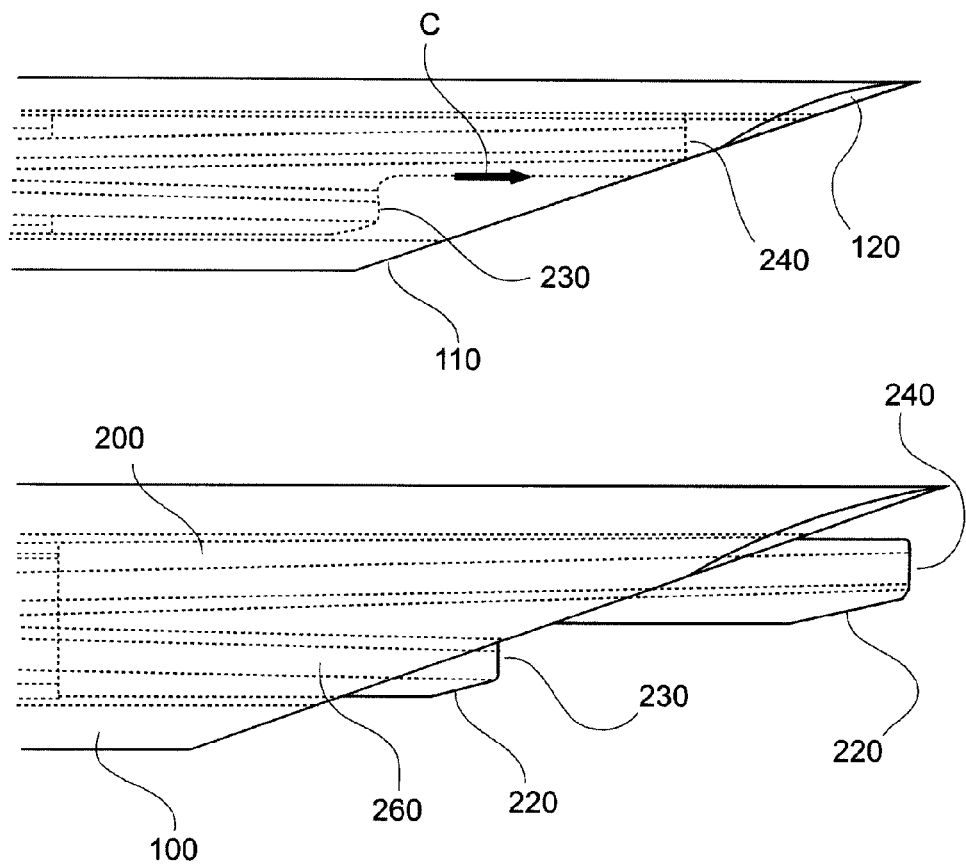
FIG. 5 shows a tip portion of a needle device according to a third embodiment of the invention, with the insert in a first and a second condition, respectively.

A third embodiment of a distal end portion of the insert 200 is shown in FIG. 5. Here, the front surface of the insert 200 comprises a blunt portion 240 as a distal tip, followed (in a direction from distal to proximal) by a bevelled portion 220, a stepped portion 230 and a further bevelled portion 220. By the stepped portion 230, a surface oriented in an axial direction of the insert and a surface transverse to the axial direction is formed. In this embodiment, channels 260 are located so that both channels ends at a surface transverse to the axial direction, one of the channels ends at the blunt portion 240 and the other one of the channels ends at the transverse surface of the stepped portion 230.

Further depicted in FIG. 5, are the position of the distal end portion of the insert 200 inside the hollow shaft, i.e. proximal to the bevel of the hollow shaft, and the position of the distal end portion of the insert outside the hollow shaft, i.e. distal to the bevel of the hollow shaft. Assuming that tissue will be in close contact with the bevel of the hollow shaft, when the hollow shaft is introduced into the tissue, the two transverse surfaces of the front surface of the insert, and thus the end surfaces of fibers located within the channels 260, can be pressed in reliably in contact with the tissue, thus ensuring good optical measurements.

The insert may be produced in mass production. Producing straight cut fibers may be done in batches. Assembling fibers in the multilumen may be well controlled making these needles compatible with mass production. Furthermore, because of this way of assembling, a rather low cost needle may be assured.

Figure 6:
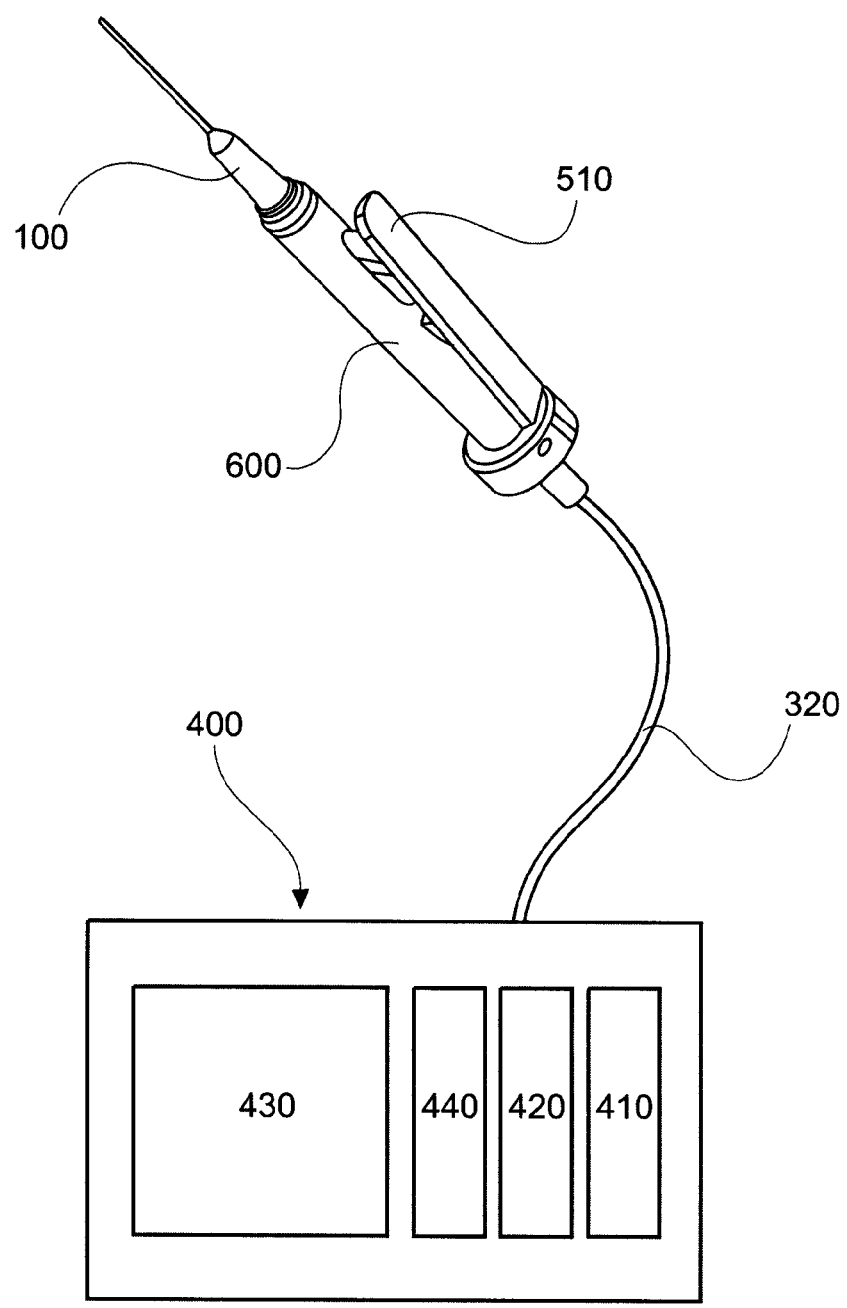
FIG. 6 shows a needle device according to the invention including a console.

As illustrated in FIG. 6, the needle with hollow shaft 100 and insert including at least one fiber may be connected to an optical console 400. The optical console comprises a light source 410 enabling light to be provided via one or more of the fibers to the tip of the insert at the distal end of the needle device. The scattered light is collected by one or more fiber and is guided towards at least one detector 420. The amount of reflected light measured at the "detection" fiber, is determined by the absorption and scattering properties of the probed structure (e.g. tissue). The data may be processed by a processing unit 440 using a dedicated algorithm. For diffuse reflectance measurements, either the light source or the detector or a combination of both must provide wavelength selectivity. For instance, light can be coupled out of the distal tip through at least one fiber, which serves as a source, and the wavelength is swept from e.g. 500-1600 nm, while the light detected by at least one detection fiber is sent to a broadband detector. Alternatively, broadband light may be provided by at least one source fiber, while the light detected by at least one detection fiber is sent to a wavelength-selective detector, e.g. a spectrometer.

For a detailed discussion on diffuse reflectance measurements see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010).

For fluorescence measurements the console must be capable of providing excitation light to at least one source fiber while detecting tissue-generated fluorescence through one or more detection fibers. The excitation light source may be a laser (e.g. a semiconductor laser), a light-emitting diode (LED) or a filtered light source, such as a filtered mercury lamp. In general, the wavelengths emitted by the excitation light source are shorter than the range of wavelengths of the fluorescence that is to be detected. It is preferable to filter out the excitation light using a detection filter in order to avoid possible overload of the detector by the excitation light. A wavelength-selective detector, e.g. a spectrometer, is required when multiple fluorescent entities are present that need to be distinguished from each other.

In case fluorescence measurements are to be combined with diffuse reflectance measurements, the excitation light for measuring fluorescence may be provided to the same source fiber as the light for diffuse reflectance. This may be accomplished by, e.g., using a fiber switch, or a beam splitter or dichroic beam combiner with focusing optics. Alternatively, separate fibers may be used for providing fluorescence excitation light and light for diffuse reflectance measurements.

Although diffuse reflectance spectroscopy is described above to extract tissue properties also other optical methods may be envisioned like diffuse optical tomography by employing a plurality of optical fibers, differential path length spectroscopy, Raman spectroscopy. Furthermore, the system may also be employed when contrast agents are used instead of only looking at autofluorescence.

In accordance with the invention an algorithm may be utilized to derive optical tissue properties such as the scattering coefficient and absorption coefficient of different tissue chromophores: e.g. hemoglobin, oxygenated haemoglobin, water, fat etc. These properties are different between normal healthy tissue and diseased (cancerous) tissue.

Figure 7:
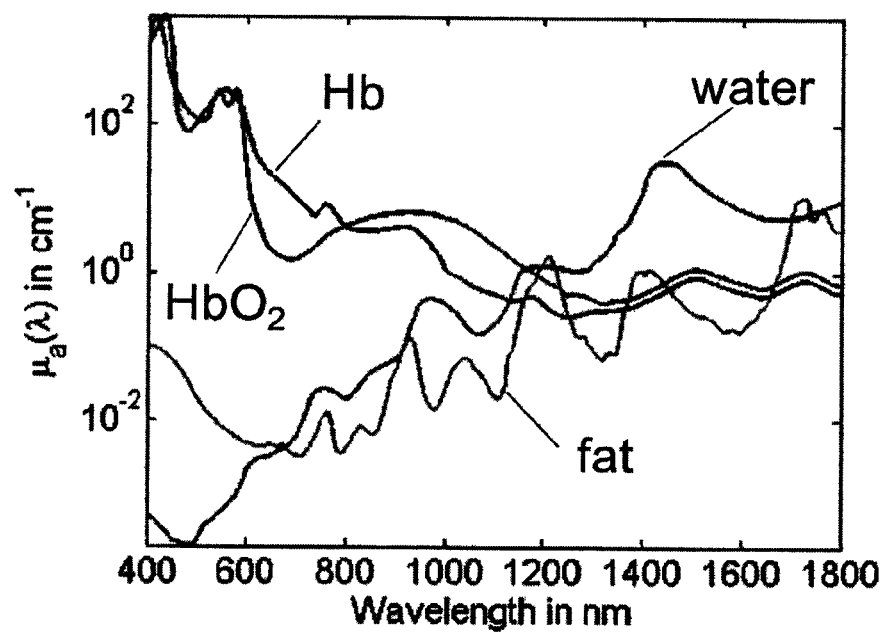
FIG. 7 shows the absorption of different biological chromophores.

The main absorbing constituents in normal tissue dominating the absorption in the visible and near-infrared range are blood (i.e. hemoglobin), water and fat. In FIG. 7 the absorption coefficient of these chromophores as a function of the wavelength are presented. Note that blood dominates the absorption in the visible range, while water and fat dominate in the near infrared range.

The total absorption coefficient is a linear combination of the absorption coefficients of for instance blood, water and fat (hence for each component the value of that shown in FIG. 7 multiplied by its volume fraction). By fitting the model to the measurement while using the power law for scattering (see R. Nachabe, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010)) we may determine the volume fractions of the blood, water and fat as well as the scattering coefficient. With this method we may now translate the measured spectra in physiological parameters that may be used to discriminate different tissues.

Another way to discriminate differences in spectra is by making use of a principal components analysis. This method allows classification of differences in spectra and thus allows discrimination between tissues. It is also possible to extract features from the spectra.

How to extract the intrinsic fluorescence from the measured fluorescence may be found for instance in Zhang et al., Optics Letters 25 (2000) p 1451.

The needles device according to the invention may be used in minimally invasive needle interventions such as low-back pain interventions or taking biopsies in the field of cancer diagnosis or in case where tissue characterization around the needle is required.

While the invention has been illustrated and described in detail in the drawings and foregoing description, such illustration and description are to be considered illustrative or exemplary and, not restrictive; the invention is not limited to the disclosed embodiments. Other variations to the disclosed embodiments may be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication sys-

LIST OF REFERENCE SIGNS 100 hollow shaft
110 bevel
120 facet
200 elongated insert
210 front surface
220 beveled portion
230 stepped portion
240 blunt portion
250 slider
260 channel
300 optical fiber
310 front surface
320 cable
400 console
410 light source
420 light detector
430 monitor
440 processing unit
500 operating mechanism
510 first lever
512 pivot of first lever
520 second lever
522 first pivot of second lever
524 second pivot of second lever
530 bearing
540 switch
550 elastic element
600 housing

The invention claimed is:

1. A needle device comprising:
a hollow shaft having a first distal end portion with a bevel, an elongated insert having a second distal end portion and being movably arranged within the hollow shaft, wherein the second distal end portion of the elongated insert comprises a front surface with at least one of a beveled portion, a stepped portion and a blunt portion;
a first optical fiber having a front surface, wherein the front surface is arranged at the front surface of the elongated insert;
operating means being shiftable between a first condition and a second condition, wherein the operating means is interconnected with the elongated insert, so that the second distal end portion is located within the hollow shaft and proximally to the bevel, when the operating means is in the first condition, and that the second distal end portion is located outside the hollow shaft and distally to the bevel, when the operating means is in the second condition; and
a switch configured to trigger an optical measurement though the first optical fiber in response to shifting of the operating means between the first and second conditions.

2. The needle device of claim 1, further comprising a second optical fiber with a front surface, wherein the front surface of the second fiber is arranged at the front surface of the elongated insert, wherein the front surface of the first optical fiber is arranged distally relative to the front surface of the second optical fiber.

3. The needle device of claim 2, further comprising:
a console including a light source, a light detector and a processing unit or processing signals provided by the light detector, wherein one of the light source and the light detector is connected with the first optical fiber and the other one of the light source and the light detector is connected with the second optical fiber.

4. The needle device of claim 1, wherein the operating means includes elements of at least one of an electromagnetic drive and an electrically driven mechanical drive.

5. The needle device of claim 1, wherein the operating means includes elements for manually shifting the operating means between the first condition and the second condition.

6. The needle device of claim 1, wherein the operating means includes a first lever and a second lever, wherein the first lever is rotatable between the first condition and the second condition, and wherein the second lever is arranged between the first lever and the elongated insert, so that a rotational movement of the lever is converted in a translational movement of the elongated insert.

7. The needle device of claim 1, wherein the elongated insert is spring-biased in a direction to a position in which the second distal end portion of the elongated insert is located within the hollow shaft and proximally to the bevel of the hollow shaft.

8. The needle device of claim 1, further comprising at least one bearing for supporting a translational movement of the elongated insert within the hollow shaft.

9. The needle device of claim 1, further comprising:
a console including a light source, a light detector and a processing unit for processing signals provided by the light detector, wherein the light source and the light detector are connected with the first optical fiber.

10. The needle of claim 1, wherein the switch activates the optical measurement when the operating means is in the second condition.

11. A needle device comprising:
a hollow shaft having a first distal end portion with a bevel, an elongated insert having a second distal end portion and being movably arranged within the hollow shaft, wherein the second distal end portion of the elongated insert comprises a front surface with at least one of a beveled portion, a stepped portion and a blunt portion;
a optical fiber having a front surface, wherein the front surface is arranged at the front surface of the elongated insert;
an operating lever being shiftable between a first condition and a second condition, wherein the operating lever is interconnected with the elongated insert such that the second distal end portion is located within the hollow shaft and proximally to the bevel when the operating lever is in the first condition, and that the second distal end portion is located outside the hollow shaft and distally to the bevel when the operating lever is in the second condition; and
a switch configured to trigger an optical measurement though the first optical fiber in response to shifting of the operating means between the first and second conditions.

12. The needle device of claim 11, further comprising a further lever, wherein the lever is rotatable between the first condition and the second condition, and wherein the further lever is arranged between the lever and the elongated insert such that a rotational movement of the lever is converted in a translational movement of the elongated insert.

13. The needle device of claim 11, wherein the elongated insert is spring-biased in a direction to a position in which the second distal end portion of the elongated insert is located within the hollow shaft and proximally to the bevel of the hollow shaft.

* * * * *